US011275076B2

(12) United States Patent
Yuan et al.

(10) Patent No.: US 11,275,076 B2
(45) Date of Patent: Mar. 15, 2022

(54) SYSTEMS AND METHODS FOR ASSESSING BLOOD PLATELET FUNCTION

(71) Applicant: Medtronic, Inc., Minneapolis, MN (US)

(72) Inventors: Charlene Yuan, Woodbury, MN (US); Trevor Huang, Maple Grove, MN (US); Tessy Kanayinkal, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 602 days.

(21) Appl. No.: 15/383,995

(22) Filed: Dec. 19, 2016

(65) Prior Publication Data

US 2018/0172665 A1    Jun. 21, 2018

(51) Int. Cl.
*G01N 33/49*    (2006.01)
*G01N 15/05*    (2006.01)

(52) U.S. Cl.
CPC ......... *G01N 33/4905* (2013.01); *G01N 15/05* (2013.01)

(58) Field of Classification Search
None
See application file for complete search history.

(56) References Cited

U.S. PATENT DOCUMENTS

| | | | |
|---|---|---|---|
| 4,752,449 A | 6/1988 | Jackson et al. | |
| 5,174,961 A | 12/1992 | Smith | |
| 5,314,826 A | 5/1994 | Baugh | |
| 5,541,892 A | 7/1996 | Kobayashi et al. | |
| 5,629,209 A * | 5/1997 | Braun, Sr | G01N 11/105 422/547 |
| 5,925,319 A | 7/1999 | Baugh et al. | |
| 5,951,951 A | 9/1999 | Lane et al. | |
| 6,010,911 A | 1/2000 | Baugh et al. | |
| 6,232,127 B1 | 5/2001 | Lane et al. | |
| 6,472,161 B1 | 10/2002 | Baugh | |
| 6,555,066 B2 | 4/2003 | Baugh et al. | |
| 6,613,286 B2 * | 9/2003 | Braun, Sr | G01N 33/4905 422/554 |
| 8,921,115 B2 * | 12/2014 | Yuan | G01N 33/4905 422/73 |

OTHER PUBLICATIONS

Carroll et al. Blood, vol. 57, No. 1, p. 44-48, 1981.*
Detwiller et al. The American Journal of Physiology, 203:107-110, 1962.*
Zida et al. Small, 2016, 12, No. 29, 3926-3934.*
Tutwiler, Valerie, et al., "Kinetics and mechanics of clot contraction are governed by the molecular and cellular composition of the blood," Blood, vol. 127, No. 1, pp. 13 (Jan. 2016)(Originally published online Nov. 24, 2015).

* cited by examiner

*Primary Examiner* — Michael L Borin
(74) *Attorney, Agent, or Firm* — Dicke, Billig & Czaja, PLLC

(57) ABSTRACT

A method carried out by a system configured to analyze blood. The method includes causing a ferromagnetic object to move in a chamber housing blood after clot initiation has been implicated. Movement of the object in the chamber is detected. The detected movement of the object is correlated with clot retraction of the blood. In some embodiments, the stop of detecting movement includes allowing the object to drop from a raised position and detecting a drop distance of the object. In related embodiments, the step of correlating detected movement with clot retraction includes reviewing a trace generated by a plurality of drop distances over time. In yet other embodiments, methods of the present disclosure can further including evaluating platelet function of the blood based upon assessed clot retraction.

13 Claims, 6 Drawing Sheets

SYSTEMS AND METHODS FOR ASSESSING BLOOD PLATELET FUNCTION

BACKGROUND

The present disclosure relates to systems and methods for evaluating or assessing blood. More particularly, it relates to systems and methods for assessing blood platelet function, for example blood platelet function of a perioperative patient.

A number of apparatuses or systems for providing point-of-care analysis of blood clotting are available. These apparatuses are configured to provide valuable information regarding blood clotting, platelet function and bleeding complications. Such apparatuses are useful in a variety of circumstances such as before or during surgery to assist in determining or maintaining appropriate levels of anticoagulant therapy, or following therapy to determine blood status following discontinuation of anticoagulant therapy. However, additional or reconfigured apparatuses that provide for easy testing or additional information are desirable.

For example, easy, informative and accurate analysis of blood clotting and platelet function can be important for patients exhibiting abnormal bleeding post-cardiopulmonary bypass. Although more than half of such patients can exhibit abnormal bleeding due to incomplete surgical homeostasis, which is often corrected by exploration, a large number of such patients exhibit abnormal bleeding because of acquired platelet dysfunctions, consumptive coagulopathy, heparin rebound, protamine excess, primary fibrinolysis, etc. Accordingly, acquiring information regarding platelet function and bleeding complications could help to identify a cause of abnormal bleeding that is not the result of incomplete surgical hemostasis and reduce the reoperation rate.

In recent years, perioperative uses of viscoelastic methods to diagnose coagulopathy bleeding, such as thrombelastography have been proven to reduce transfusion of allogenic blood products and result in substantial cost savings. Some systems and methods, such as those provided in U.S. Pat. Nos. 6,555,066 and 6,232,127 evaluate the effect of platelet inhibitors or activators based on determined relative clotting time. However, clotting time is not specific to platelet function because clotting time is measure by clot viscosity change. While clot viscosity change is a good indicator of clot initiation, it is not truly indicative of overall platelet function. Other systems and methods, such as those described in U.S. Pat. No. 8,921,115, the teachings of which are incorporated by reference herein in their entirety, evaluate all phases of the coagulation cascade, but may not provide for optimal platelet function assessment.

SUMMARY

The inventors of the present disclosure recognized that a need exists for systems and methods for assessing blood platelet function of a patient.

Some aspects of the present disclosure are directed toward a method carried out by a system configured to analyze blood. The method includes causing a ferromagnetic object to move in a chamber housing blood after clot initiation has been implicated. Movement of the ferromagnetic object in the chamber is detected. Finally, the detected movement of the ferromagnetic object in the chamber is correlated with clot retraction of the blood. In some embodiments, the step of causing the object to move includes raising the ferromagnetic object within the blood, and the stop of detecting movement of the object includes allow the object to drop from the raised position and detecting a distance the object subsequently drops. In some embodiments the steps of raising, dropping and detecting the corresponding drop distance constitute a test cycle, and the method further includes repeating the test cycle to obtain a plurality of drop distances over time. In related embodiments, the step of correlating detected movement with clot retraction includes reviewing a trace generated by the drop distances over time. In yet other embodiments, methods of the present disclosure can further including evaluating platelet function of the blood based upon assessed clot retraction and optionally based upon additional parameters such as clot strength.

Other aspects of the present disclosure are directed toward a non-transitory computer-readable medium programmed with instructions that, when executed, cause a system to carry out one or more of the methods above.

Yet other aspects of the present disclosure are directed toward a system for analyzing blood. The system includes a chamber, a ferromagnetic object, a detector and electronics. The chamber is configured for housing blood. The ferromagnetic object is movably disposed within the chamber. The detector configured to detect a position of the ferromagnetic object within the chamber. The electronics are operably coupled to the ferromagnetic object (e.g., via an electromagnet) and the detector. The electronics are configured to control movement of the ferromagnetic object within the chamber. The electronics are further configured to initiate movement of the ferromagnetic object within the first chamber upon receiving information indicative of clot initiation of the blood, followed by allowing the first ferromagnetic object to drop within the first chamber. The electronics are even further configured to detect a drop distance of the first ferromagnetic object, the drop distance being indicative of clot retraction. In some embodiments, the system further includes a second chamber within with a second ferromagnetic object is moveably maintained, the electronics being configured to determine clot initiation based upon movement of the second ferromagnetic object within blood housed in the second chamber.

DETAILED DESCRIPTION

Figure 1:
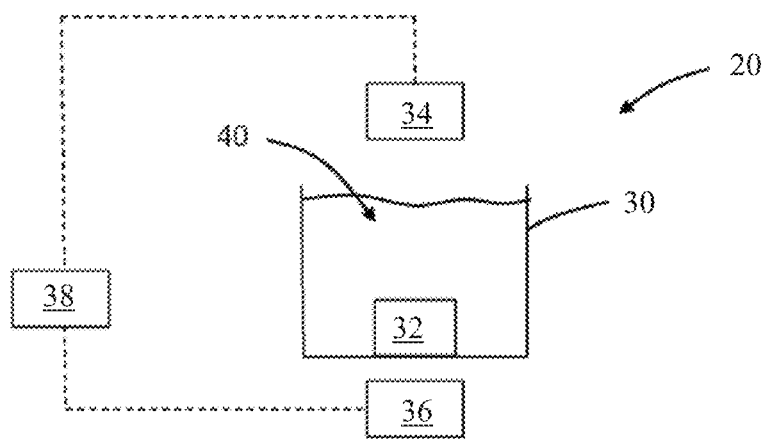
FIG. 1 is a schematic drawing of selected components of a blood analysis system in accordance with principles of the present disclosure.

As used herein, "clot retraction" is the shrinking of a blood clot over a period of time. Clot retraction is dependent on release of multiple coagulation factors from platelets trapped in the fibrin mesh of the clot.

As used herein, determining or correlating "clot retraction" means performing a calculation or estimation that employs a parameter indicative of clot retraction that occurs after initiation of clot formation to determine or correlate the parameter to the retraction of the clot.

As used herein, a clot is determined to be "fully formed" when an object disposed in blood moves a distance or velocity that is lower than a predetermined distance or velocity or when energy configured to cause the object to move within the blood exceeds a predetermined threshold value without moving the object to a predetermined distance or rate.

As used herein, a "predetermined" threshold value is a value that is determined prior to the time in which it is compared to another value. The value may be based on baseline data obtained earlier in time that the value to which it is being compared, may be a value placed in memory prior to analysis, or the like.

Aspects of the present disclosure provide systems and methods for assessing clot retraction of blood based upon sensed or detected information indicative of clot retraction. In some embodiments, clot retraction is correlated with changes in distance an object moves within blood over time. In some embodiments, the systems and methods of the present disclosure provide for platelet function evaluation based on assessed clot retraction and optionally further based upon strength of clotting, for example as correlated with amount of energy employed to move an object within blood. In yet other embodiments, the systems and methods of the present disclosure provide for additional blood parameter evaluations. In some embodiments, clot retraction is determined by a system in which a ferromagnetic material is moved within blood.

In embodiments, the methods described herein are employed by, or the systems described herein include, any suitable system or apparatus for analyzing blood clotting. For example, plunger-type systems or apparatuses such as those described in U.S. Pat. Nos. 6,010,911; 5,174,961; 4,752,449; 5,951,951; 5,925,319; 5,314,826; and 5,541,892; systems or apparatuses that employ ferromagnetic particles or objects moved by electromagnets such as those described in U.S. Pat. Nos. 5,626,209; 6,613,286; and 8,921,115; or the like may be employed in accordance with principles of the present disclosure or may be modified to perform the methods described herein. Each of the afore-mentioned patents is hereby incorporated by reference in their respective entirety to the extent that it does not conflict with the disclosure presented herein. In aspects, the description presented herein is tailored to systems and apparatuses that employ ferromagnetic particles or objects moved by electromagnets. However, it should be understood that other suitable systems and apparatuses, in many cases, may be used to carry out the methods described herein.

Regardless of the type of system employed, a blood analysis system of the present disclosure includes at least one chamber or container into which blood may be placed for analysis. The system is typically configured to mix the blood with one or more substances that may affect clotting of the blood. For example, the system may employ sonic, ultrasonic or other waves, washers, plungers, rods, or the like to mix the blood and one or more substances. The substances or agitation of blood may facilitate clotting of the blood. The system is configured to detect or monitor changes in clot size or clot reduction, and optionally correlate such changes with platelet function. For example, the system may include one or more detectors for monitoring waves, monitoring position or rate of movement of an object such as a plunger or a washer, monitoring relative phase of a rod, or the like to assess whether clot size has changed. Other parameters, such as clotting status, the amount of time for blood clotting to occur (often referred to as activated clotting time), etc., may also be determined or assessed. The system may include a second (or more) chamber configured to contain blood and components for evaluating clotting status of the blood contained in the second chamber.

Figure 2:
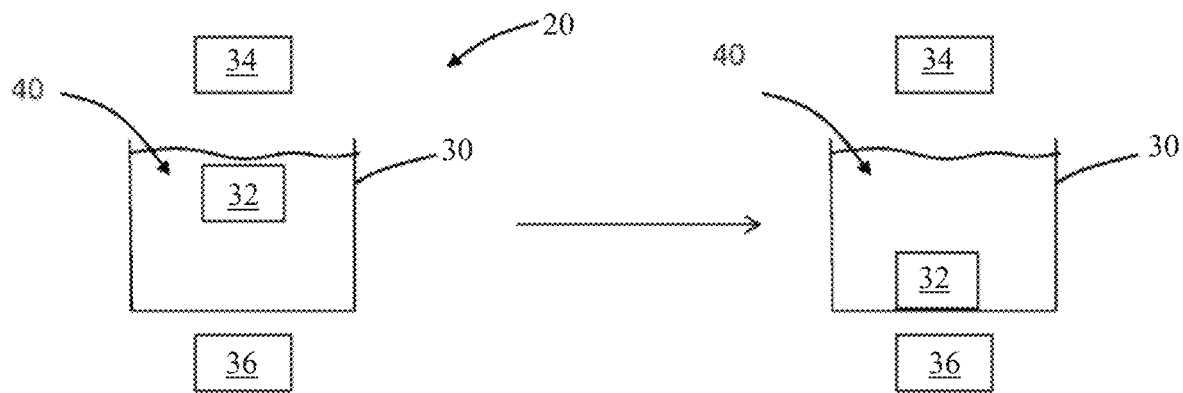
FIG. 2 is a schematic drawing of selected components of the system of FIG. 1 and illustrating stages of operation thereof.

By way of example and with reference to FIGS. 1 and 2, schematic drawings of selected components of an example of a blood analysis system 20 are shown. The system 20 includes a chamber 30, a ferromagnetic object 32, an electromagnet 34, at least one sensor 36, and electronics 38. The chamber 30 is configured to contain blood 40 to be assessed or tested. The object 32 is moveable within the blood 40 as contained within the chamber 30. In some embodiments, the system 20 is configured such that the chamber 30 remains stationary during a testing process. In this regard, the object 32 is movable against gravity by the electromagnet 34, which is operably coupled to electronics 38. The electronics 38 are configured to control activation of the electromagnet 34. The object 32 may be moved against gravity and the position (and optionally other parameters such as rate of movement) of the object 32 within the chamber 30 may be detected by the sensor 36, which is also operably coupled to the electronics 38.

The electronics 38 can include a processor, memory, user interface, timer or counter, power source or the like. The electronics 38 can include any suitable processor, such as one more microprocessors, DSPs, ASICs, FPGAs, programmable logic circuitry, or the like, and the functions attributed to the processor herein may be embodied as hardware, firmware, software or any combination thereof. Memory can store instructions that cause the processor to provide the functionality ascribed to a system or apparatus described herein, and can store information used by the processor to provide the functionality ascribed to a system or apparatus described herein. Memory can include any fixed or removable magnetic, optical, or electronic media, such as RAM, ROM, CD-ROM, hard or floppy magnetic disks, EEPROM, or the like. Memory may also include a removable memory portion that may be used to provide memory updates or increases in memory capacities. A power source can deliver operating power to components of a system or apparatus described herein. Power sources may be an AC or DC power source, such as a battery and a power generation circuit to produce the operating power.

Still with reference to FIGS. 1 and 2, the object 32 can be caused to move upwardly within the blood 40 via the electromagnet 34 (as operated, for example, by the electronics 36) to a position akin to that at the left in FIG. 2. When the electromagnet 34 is subsequently deactivated or de-energized, the object 32 can then fall within the blood 40 under the force of gravity, for example to or toward the position implicated at the right in FIG. 2. Clots formed in or by the blood 40 can affect the distance the object 32 drops (e.g., travels or falls) within the blood 40 due to gravity, including, for example an absolute drop distance, drop distance at the end of a predetermined time period, or rate of drop. Moreover, as the clot(s) experiences clot retraction, the corresponding effect on drop distance will change. Stated otherwise, an initiated, fully formed clot residing at an underside of the object 32 resists downward movement of the object 32 within the blood 40 (from the position to the left in FIG. 2), thus acting to limit the distance the object 32 will drop within the blood 40 and/or decrease the rate at which the object 32 drops. After experiencing clot retraction, that same clot (again residing at an underside of the object 32) may again resist downward movement of the object 32 within the blood (from the position of FIG. 2), but to a lesser extent as compared to the initiated, fully formed state. As a result, the distance the object 32 drops and/or the rate at which the object 32 drops increases following clot retraction (at least as compared to the initiated, fully formed clot). The electronics 38, based on data from the sensor 36, are configured to determine the drop distance the object 32 falls and optionally the velocity at which the object 32 falls. The electronics 38 can be further configured to assess clot retraction by, for example, evaluating or comparing drop distance values obtained over time. The electronics 60 can further be configured to assess platelet function based upon the assessed clot retraction as described below. As mentioned above, additional information regarding the blood can be optionally be obtained or assessed by the electronics 38 in accordance with the systems and methods of the present disclosure, such as those described in U.S. Pat. Nos. 5,626,209; 6,613,286; and 8,921,115.

Unlike previously described systems and apparatuses employing a moveable ferromagnetic object 32, such as a washer, the systems, apparatus and methods described herein are configured to evaluate or assess clot retraction and optionally platelet function based upon assessed clot retraction, in addition to or alternatively to activated clotting time and strength of clotting. Additional detail regarding embodiments of methods that may be employed by such systems and apparatuses will be discussed below.

Figure 3:
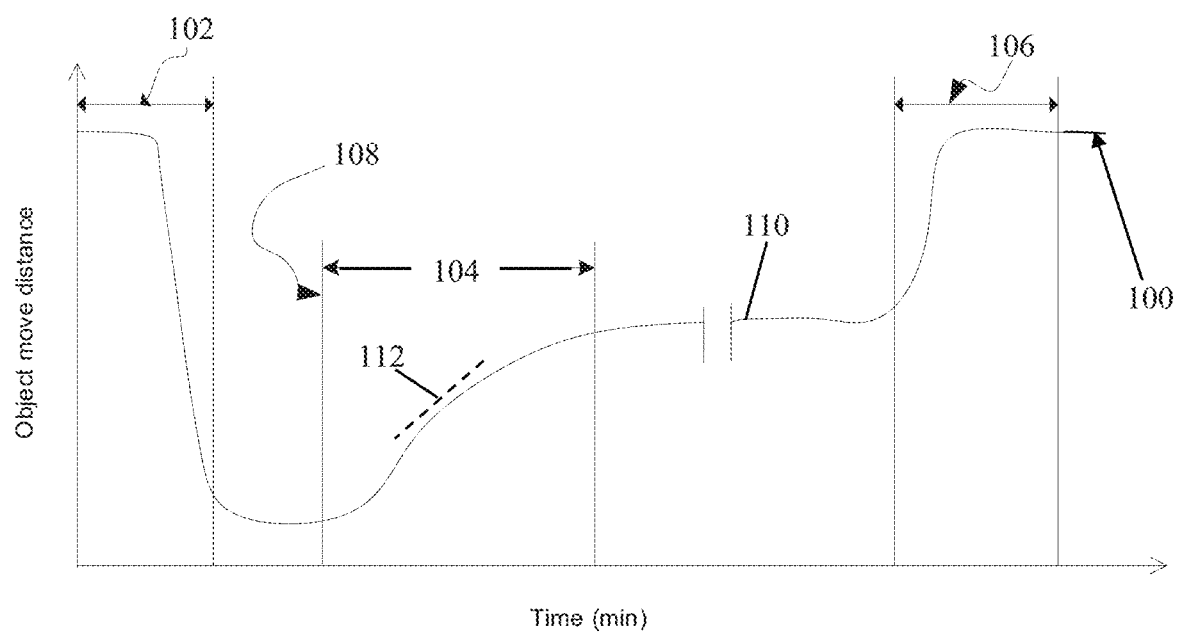
FIG. 3 is a schematic drawing of a predicted trace of drop distances of an object over time that may be representative of data obtainable by systems and methods of the present disclosure.

Referring now to FIG. 3, a schematic drawing of a predicted trace 100 generated by successive drop distance test cycles of an object (e.g., the ferromagnetic object 32 described above) in blood over time that may be representative of data obtainable by an embodiment of a blood analysis system or apparatus of the present disclosure (e.g., the blood analysis system 20 of FIGS. 1 and 2). For example, and with additional reference to FIGS. 1 and 2, each test cycle includes the object 32 caused to move by the electromagnet 34 toward the top of the chamber 30 and then allowed to drop; the drop distance of the object 32 is determined or sensed (e.g., an absolute drop distance is determined or sensed once the object 32 is at rest within the blood 40, or is determined or sensed at the end of a predetermined test cycle period). This so-determined drop distance serves as a single data point on the trace 100. The same drop distance test cycle is repeated for the same blood sample 40, at regular or irregular time intervals, over the course of an assessment time period with the result of each successive drop distance test cycle providing an additional data point from which the trace 100 is generated. (i.e., the determined "object drop distance" is plotted relative to the Y-axis at the corresponding point in time over the assessment time period along the X-axis).

The depicted trace 100 illustrates data predicted to be obtained during activated clotting 102, clot retraction 104 and fibrinolysis 106. Before the blood 40 begins to coagulate (i.e., starting at Time 0), the distance the object 32 falls within the blood 40 with each drop distance test cycle is relatively substantial, and remains relatively constant. However, as the blood begins to coagulate and clot, the distance the object 32 falls within the blood 40 with each successive drop distance test cycle begins to decrease. It can be possible to designate or calculate the activated clotting time 102, for example based upon the time at which the drop distance decreases by a certain percentage or amount of baseline or initial drop distance (at Time 0). As shown, the drop distance of later drop distance test cycles is predicted to decrease until the blood is fully clotted (represented by a trough in the trace 100), and can be viewed as establishing a minimum drop distance. As the blood clot(s) then begin to retract, the distance the object 32 falls within the blood with each successive drop distance test cycle begins to increase. Initiation of the clot retraction phase is designated at 108. The time at which the drop distance increases by a certain amount or percentage from the minimum drop distance may be used to determine the clot retraction time 104. As shown, the drop distance of later drop distance test cycles is predicted to increase with further clot retraction to an approximate plateau 110 that defines a plateau drop distance. A slope 112 of the trace along the region of the clot retraction time 104 can be used to characterize or assess clot retraction. For example, larger magnitude slopes can be predicted to be indicative of more rapid clot retraction. Also, an area under the curve (AUC) in the region of the clot retraction time 104 indicates extent of clot retraction. After a further period of time, the clot(s) will begin to lyse and the blood will become less viscous. As a result, the distance the object 32 falls within the blood with each successive test cycle begins to substantively increase from the plateau drop distance. The time at which the drop distance increase by a certain amount or percentage from the plateau drop distance may be used to determine the fibrinolysis time 106.

Figure 4:
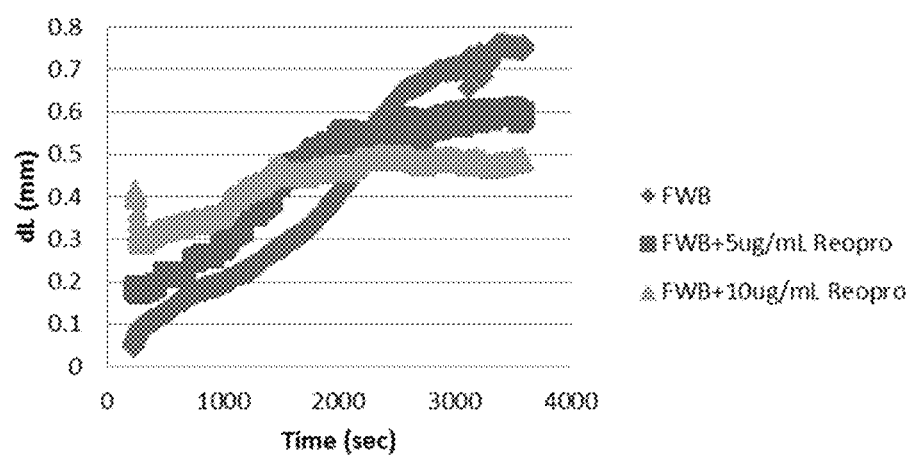
FIG. 4 is a plot of drop distance test results over time for three blood samples.

Regardless of any additional information obtained, it has surprisingly been found that in some embodiments, the systems and methods of the present disclosure can utilize the clot retraction assessment or information as described above in generating an evaluation or assessment of platelet function. As a point of reference, FIG. 4 presents the results of the drop distance cycle tests described above (using a ferromagnetic washer as the object) with three different blood samples. The first blood sample ("FWB") consisted of fresh whole blood. The second blood sample ("FWB+5 ug/mL Reopro") consisted of the fresh whole blood of the first sample and the platelet inhibitor Reopro at a concentration of 5 µg/mL. The third blood sample ("FWB+10 ug/ML Reopro") consisted of the fresh whole blood of the first sample and the platelet inhibitor Reopro at a concentration of 10 µg/mL. Thus, first blood sample had no platelet inhibitor added; the third blood sample had a platelet inhibitor at a higher concentration that the second blood sample. With each of the three blood samples, the drop distance cycle tests began after clot formation was assumed to have initiated. As shown, the first blood sample (FWB, no platelet inhibitor) exhibited minimal object movement at clot initiation, and incrementally greater object movement over time due to clot retraction as compared to the second and third samples (each with platelet inhibitor). In the clot retraction phase, then, the first blood sample (with normal platelet function) showed greater clot retraction that the second and third blood samples (each with abnormal platelet function due the presence of the platelet inhibitor). A comparison of the second and third blood samples further revealed that the object movement profile is platelet inhibitor dose dependent. From this review, it was surprisingly found that platelet retraction is an indicator of platelet function. As explained in U.S. Pat. No. 8,921,115, clot strength can be another indicator of platelet function, and can be assessed (along with platelet retraction) with some systems and methods of the present disclosure.

Figure 5:
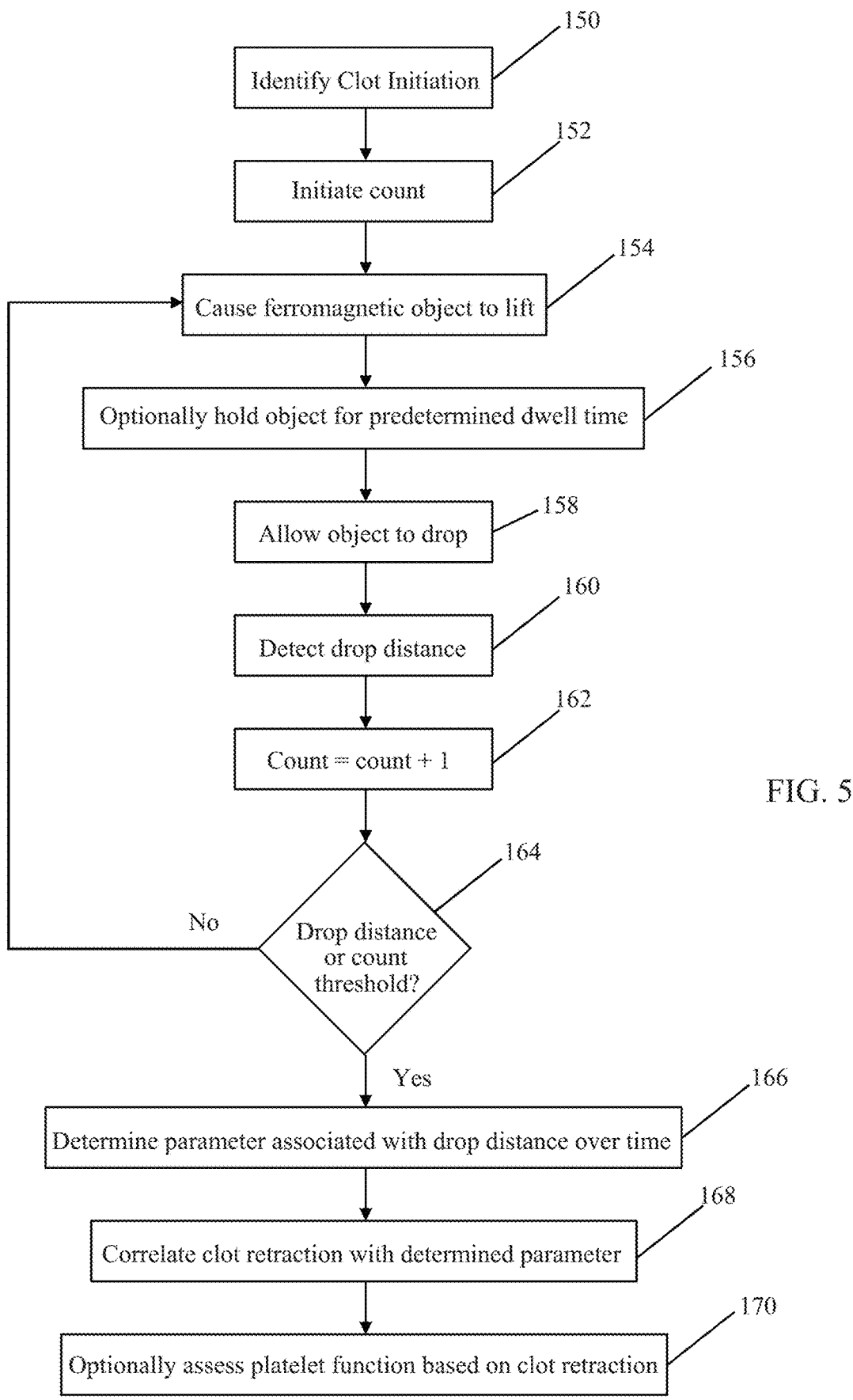
FIG. 5 is a flow diagram of a method in accordance with principles of the present disclosure.

Referring now to FIG. 5, an overview of a method for determining clot retraction is depicted. The method includes identifying clot initiation or start of activated clotting time of blood housed in a first chamber at step 150. Identification of clot initiation can be performed in various manners, for example by repeatedly moving a ferromagnetic object (e.g., washer) in the first chamber, detecting a rate of movement of the object through the blood, and determining whether the position or velocity of the object is indicative of clot initiation (e.g., determining whether the movement has declined a predetermined amount or percentage relative to baseline or has decreased below a threshold value that has been determined to be indicative of clot initiation) as also described in U.S. Pat. No. 8,921,115, the teachings of which are incorporated herein by reference in its entirety. In yet other embodiments, and as described in greater detail below, a second chamber housing a volume of the same blood as in the first chamber can be utilized (along with a ferromagnetic object) to identify activated clotting time. Yet other techniques that may or may not entail movement of a ferromagnetic object in the blood as known to those of ordinary skill can be used to identify activated clotting time.

Upon identifying initiation of activated clotting time, a clot retraction assessment phase begins, and a counter or timer (or both) is initiated at step 152. At step 154, an object, such as a ferromagnetic object (e.g., ferromagnetic washer) is caused to move in the first chamber (e.g., by activating an electromagnet as described above). For example, the ferromagnetic object is caused to move upwardly or lift within the first chamber. In some embodiments, a predetermined delay time can be implemented between the step of identifying clot initiation (step 150) and the step of causing the ferromagnetic object to move (step 154). Optionally, at step 156, the object is held in the moved (e.g., lifted) position for a predetermined dwell time (e.g., by maintaining the electromagnet in the activated state for the predetermined dwell time). With optional embodiments in which step 156 is performed, the predetermined dwell time can be selected based upon an expected time for clot(s) to build or form at an underside of the object. For example, the predetermined dwell time can be on the order of 2-10 seconds, optionally 3-6 seconds, and in some embodiments 4.5 seconds. Regardless, at step 158, the object is allowed to fall or drop in the blood under the force of gravity (e.g., by de-energizing or deactivating the electromagnet). The drop distance of the object is detected or determined at step 160. In some embodiments, the drop distance is detected or determined upon expiration of a predetermined drop time (e.g., via the sensor as described above). The predetermined drop time can be on the order of 0.1-5 seconds, optionally 0.2-3 seconds, and in some embodiments 0.5 seconds. In other embodiments, the drop distance is detected at step 160 once the object is deemed to be stationary within the blood. In some embodiments, the detected or determined drop distance is electronically recorded in a memory, optionally in conjunction with time elapsed from start of the clot retraction assessment phase (e.g., time elapsed following step 152).

The counter or timer is increased at step 162. The process is repeated until a drop distance threshold or count threshold has been reached at step 164. The cyclic process of lifting the object, optionally holding the lifted object for the predetermined dwell time, allowing the object to drop, and detecting or determining the drop distance may be ceased if either threshold is reached, and a parameter associated with the detected or determined drop distances over time can be calculated or determined at step 166. The parameter may be, for example, the slope or rate of change in drop distance over time. Clot retraction is then correlated with the parameter at step 168. In some non-limiting embodiments, platelet function of the blood is optionally assessed or determined based upon the assessed clot retraction, either alone or in combination with other assessed parameters, at step 170. For example, clot strength can be determined or assessed in accordance with the descriptions of U.S. Pat. No. 8,921,115 and utilized with the assessed clot retraction to determine or assess platelet function with some systems and methods of the present disclosure.

It will be understood that, while the methods depicted and described with regard to FIG. 5 are discussed herein with regard to detection of movement of an object within a given chamber, the methods may be employed with regard to systems and apparatuses that use more than one such object and one such chamber.

Figure 6:
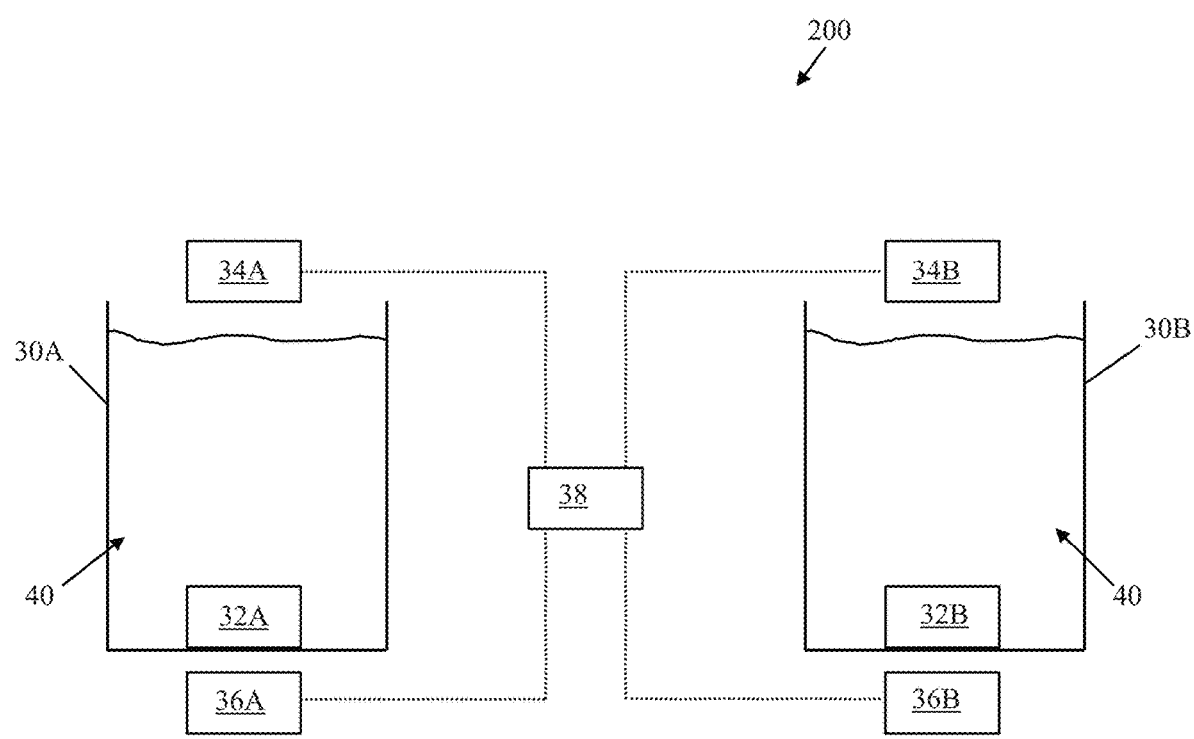
FIG. 6 is a schematic drawing of selected components of another blood analysis system in accordance with principles of the present disclosure.

In an example of a two chamber system, the first chamber may be used for at least clot retraction determination, and a second chamber with a similar mechanical configuration and chemical composition may be used to indicate clot formation and determining activated clotting time. For example, a two chamber system 200 in accordance with principles of the present disclosure is schematically shown in FIG. 6, and includes components akin to those described above in FIGS. 1 and 2. For example, the system 200 includes a first chamber 30A and a second chamber 30B. A first ferromagnetic object 32A is located within the first chamber 30A, and a second ferromagnetic object 32B is located within the second chamber 30B. The first and second chambers 30A, 30B can be identical, as can the first and second ferromagnetic objects 32A, 32B. A first electromagnet 34A is located relative to the first chamber 30A to cause movement of the first object 32A, and at least a first sensor 36A is located to detect movement or position of the first object 32A. Similarly, a second electromagnet 34B is located relative to the second chamber 30B to cause movement of the second object 32B, and at least a second sensor 36B is located to detect movement or position of the second object 32B. Electronics 38 are operably coupled to the first and second electromagnets 34A, 34B, and the first and second sensors 36A, 36B in accordance with the descriptions above.

Figure 7:
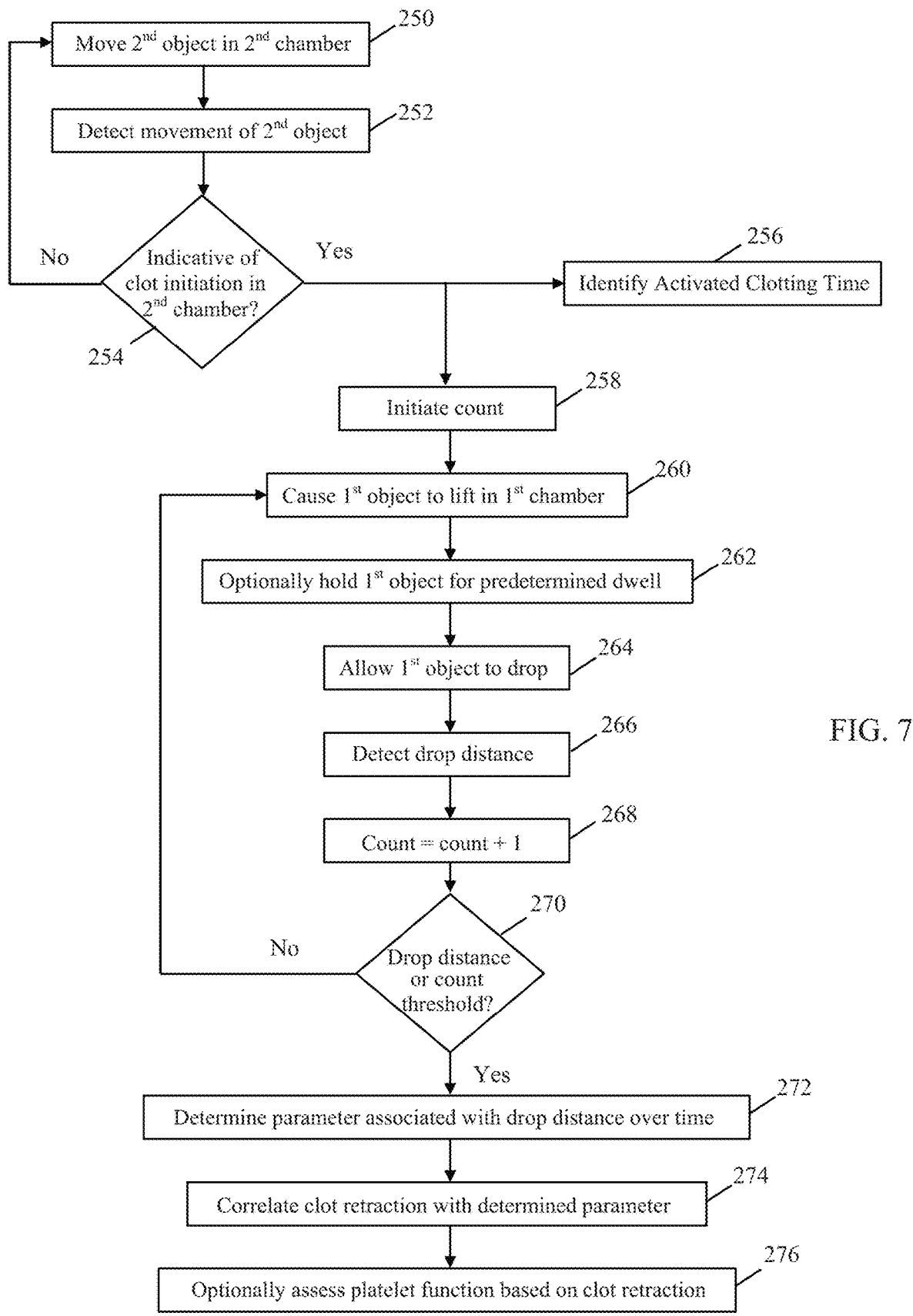
FIG. 7 is a flow diagram of another method in accordance with principles of the present disclosure.

An overview of a method for determining or assessing clot retraction using the system 200 is depicted in FIG. 7. With cross-reference between FIGS. 6 and 7, blood 40 is loaded into each of the first and second chambers 30A, 30B (i.e., a sample of a patient's blood is obtained, and a portion of this sample is loaded into the first chamber 30A and the second chamber 30B). In some embodiments, one or more mixing operations are optionally performed on the blood 40 in both of the chambers 30A, 30B; if mixing is desired, identical mixing operations (e.g., agitation, chemistry, etc.) are performed on the blood 40 in both chambers 30A, 30B. Regardless, the method includes operating the second electromagnet 34B to cause the second object 32B to move in the blood 40 of the second chamber 30B at step 250. At step 252, the rate of movement of the second object 32B is detected, such as the second object 32B rising or falling through the blood 40 in the second chamber 30B. The method further includes determining whether the position or velocity of the second object 32B is indicative of clot initiation at step 254. For example, by determining whether movement has declined a predetermined amount or percentage relative to baseline or has decreased below a threshold value that has been determined to be indicative of clot initiation. If the detected movement of the second object 32B is determined to not be indicative of clot initiation, the method returns to step 250 and is cyclically repeated. Once the detected movement of the second object 32B is determined to be indicative of clot indication, activated clotting time may be calculated at step 256 (e.g., by determining the length of time from start to clot initiation).

While the second object 32B is caused to move in the second chamber 30B for clot detection, the first ferromagnetic object 32A in the first chamber 30A remains stationary (e.g., rests on the bottom of the first chamber 30A). Once a clot is determined to have been initiated in the second chamber 30B (e.g., at step 254), the method proceeds to perform steps at the first chamber 30A akin to those described above with respect to FIG. 5. For example, a counter or timer (or both) is initiated at step 258. At step 260, the first object 32A is caused to lift or rise in the first chamber 30A (e.g., by activating the first electromagnet 34A as described above). In some embodiments, a predetermined delay time (e.g., 15-60 seconds) can be implemented between the step of identifying clot initiation (step 254) and the step of causing the ferromagnetic object to move (step 260), accounting for the possibility that clotting may occur slightly more rapidly in the blood 40 of the second chamber 30B (as compared to the blood 40 of the first chamber 30A) due to cycling of the second ferromagnetic object 32B (that has not otherwise been occurring with the blood 40 of the first chamber 30A). Optionally, at step 262, the first object 32A is held in the lifted position for a predetermined dwell time (e.g., 2-10 seconds, optionally 3-6 seconds, and in some embodiments 4.5 seconds). At step 264, the first object 32A is allowed to fall or drop in the blood 40 under the force of gravity (e.g., by de-energizing the first electromagnet 34A). The drop distance of the first object 32A is detected or determined at step 266. In some embodiments, the drop distance is detected or determined upon expiration of a predetermined drop time (e.g., 0.1-5 seconds, optionally 0.2-3 seconds, and in some embodiments 0.5 seconds). In some embodiments, the detected or determined drop distance is electronically recorded in a memory, optionally in conjunction with time elapsed from start of evaluation. The counter or timer is increased at step 268. The process is repeated until a drop distance threshold or count threshold has been reached at step 270. The cyclic process of lifting the first object 32A, optionally holding the lifted first object 32A for the predetermined dwell time, allowing the first object 32A to drop, and detecting or determining the drop distance may be ceased if either threshold is reached, and a parameter associated with the detected or determined drop distances over time can be calculated or determined at step 272. The parameter may be, for example, the slope or rate of change in drop distance over time. Clot retraction is then correlated with the parameter at step 274. In some non-limiting embodiments, platelet function of the blood is optionally assessed or determined based upon the assessed clot retraction, either alone or in combination with other assessed parameters, at step 276.

With the method of FIG. 7, as well as with other methods of the present disclosure making use of at least two chambers, minimizing movement of the object within the blood of the chamber at which clot retraction will be assessed prior to initiation the clot retraction testing phase can provide an improved assessment of clot retraction. For example, with the method FIG. 7, following any optional mixing operations, the first object 32A in the first chamber 30A remains stationary while clot formation is determined in the blood 40 of the second chamber 30B by moment of the second object 32B. Because the first object 32A is not moving in the blood 40 of the first chamber 30A during this clot formation testing phase, a formed clot is not compressed or disturbed by the first object 32A and increasing clot retraction exerted by platelets will occur in the blood 40 of the first chamber 30A (as compared to the blood 40 of the second chamber 30B). In other words, by minimizing movement of the first object 32A in the blood 40 of the first chamber 30A, platelets of the blood 40 of the first chamber 30A will not be damaged or destroyed prior to initiation of the clot retraction testing phase, and/or the fibrin network formed is not disturbed or compressed prior to initiation of the clot retraction testing phase.

Figure 8:
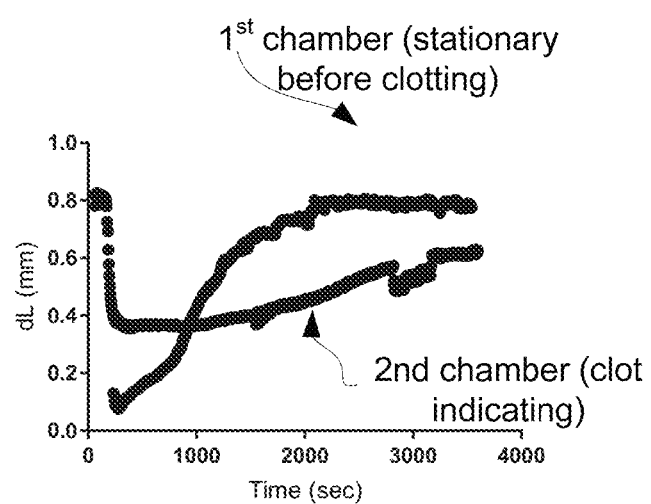
FIG. 8 is a plot of drop distance test results over time.

As a point of reference, FIG. 8 illustrates the results of tests performed on whole blood with normal platelet counts and functions. Samples of the whole blood were placed into first and second chambers, each containing a ferromagnetic washer. The washer in the second chamber was caused to move (via EMF as described above) and then allowed to drop, with the drop distance sensed or determined as described above, while the washer in the first chamber remained stationary. Cycled lifting and dropping of the washer in the second chamber was repeated to determine clot formation. At a point in time where clot formation was inferred from movement of the washer in the second chamber, the washer in the first chamber was then subjected to the same cycled drop tests (which continued to occur with the washer of the second chamber). The drop distances for both chambers over time are plotted in the graph of FIG. 8. As shown, at the start of the test, no clots were initially present in the blood of the second chamber (or the first chamber) such the second washer initially travelled the full height of the second chamber. Blood clot formation was implicated by the second chamber at approximately the three minute mark, and cycled movement of the first washer in the first chamber was initiated. As clots formed, the drop distance of the second washer decreased over time (e.g., it is surmised that clots formed on top and bottom of the second washer, effectively locking the second washer in the middle of the second chamber). At approximately the thirteen minute mark, the clot retraction process started in the second chamber, and the second washer started to move again in the second chamber. In the first chamber, the clot retraction process was found to start earlier than with the blood of the second chamber. Further, the clot retraction in the blood of the first chamber was more pronounced as compared to the blood of the second chamber, with the drop distance of the first washer exceeding that of the second washer over time. From these results, it is was surprisingly found that minimizing movement of the object within the blood of the chamber at which clot retraction is to be assessed prior to initiation of the clot retraction testing phase can provide an improved assessment of clot retraction.

The methods depicted at FIGS. 5 and 7 are merely illustrative of the methods contemplated herein. It will be understood that other similar methods are contemplated and are encompassed by the spirit of this disclosure. It will be further understood that the methods presented in FIGS. 5 and 7 are not intended to be mutually exclusive and that one or more steps depicted and described herein within one or both of FIGS. 5 and 7 may be incorporated into other methods of the present disclosure.

As mentioned above, in some embodiments of the present disclosure, the systems or apparatuses include at least one chamber or container and a ferromagnetic object located within the chamber, for example the test chamber and ferromagnetic washer constructions described in U.S. Pat. Nos. 6,613,286 and 5,629,209 ("Braun References"). The apparatuses of the Braun References incorporate a ferromagnetic washer object having dimensions of 0.125 inch (ID), 0.313 inch (OD), and 0.032 inch thickness. The corresponding chamber of the Braun References has an inner diameter approximating the outer diameter of the ferromagnetic washer. In some optional embodiments, systems of the present disclosure include the same chamber as described in the Braun References (e.g., an inner diameter on the order of 0.313 inch), and a differently-dimensioned ferromagnetic washer. In particular, the optional ferromagnetic washers of the present disclosure can have a mass akin to the mass of the ferromagnetic washers of the Braun References (so as to be acted upon as desired by the same electromagnet), but a more narrow outer diameter. For example, ferromagnetic washers of some embodiments of the present disclosure can have dimension on the order of 0.125 inch (ID), 0.201 inch (OD), and 0.064 inch thickness. Other dimensions are also envisioned. In some embodiments, the outer dimeter of the ferromagnetic washer is at least 25% less than the inner diameter of the corresponding chamber. Regardless, by providing the ferromagnetic washer to have an outer diameter substantively less than the inner diameter of the chamber, sensitivity to clot retraction detection is increased as clots are able to form or build on top, bottom and surrounding the sides of the washer.

The apparatuses, systems and methods of the present disclosure provide a marked improvement over previous designs. By providing meaningful assessment of clot retraction, a more complete evaluation of platelet function can be achieved.

Although the present disclosure has been described with reference to preferred embodiments, workers skilled in the art will recognize that changes can be made in form and detail without departing from the spirit and scope of the present disclosure.

What is claimed is:

1. A method carried out by a system configured to analyze blood, comprising:
   causing a first ferromagnetic object to move in a first chamber housing blood after clot initiation has been implicated;
   detecting movement of the first ferromagnetic object in the first chamber;
   wherein the step of causing the first ferromagnetic object to move in the first chamber followed by the step of detecting movement of the first ferromagnetic object is a test cycle;
   repeating the test cycle until occurrence of an event select from the group consisting of (i) the detected movement of the first ferromagnetic object exceeds a distance threshold and (ii) performance of a predetermined number of test cycles;
   wherein the detected movement is a distance the first ferromagnetic object drops within first chamber such that the detected movement is a drop distance, and further wherein the step of repeating the test cycle includes obtaining a plurality of drop distances over time;
   correlating the detected movement of the first ferromagnetic object in the first chamber with clot retraction of the blood, including:
      generating a trace of the plurality of drop distances over time,
      identifying an initiation of a clot retraction phase in the trace,
      identifying a plateau in the trace subsequent to the initiation of the clot retraction phase and prior to a fibrinolysis phase,
      designating a region of the trace between the initiation of the clot retraction phase and the plateau as a clot retraction time, and
      assigning a slope of the trace along the clot retraction time as an extent of clot retraction value of the blood; and
   assessing platelet function of the blood based upon the clot retraction value, wherein the step of causing the first ferromagnetic object to move in a first chamber includes causing the first ferromagnetic object to move after causing a second ferromagnetic object to move in a second chamber housing blood, detecting movement of the second ferromagnetic object in the second chamber, and determining whether the detected movement of the second ferromagnetic object is indicative of clot initiation.

2. The method of claim 1, wherein the step of causing the first ferromagnetic object to move includes causing the first ferromagnetic object to move against the force of gravity.

3. The method of claim 2, wherein the step of causing the first ferromagnetic object to move includes energizing an electromagnet associated with the chamber.

4. The method of claim 1, further comprising:
   obtaining information indicative of clot strength of the blood;
   wherein the step of assessing platelet function of the blood is further based upon the clot strength.

5. The method of claim 1, wherein the first ferromagnetic object remains stationary in the first chamber during the steps of causing a second ferromagnetic object to move, detecting movement of the second ferromagnetic object, and determining whether the detected movement of the second ferromagnetic object is indicative of clot initiation.

6. The method of claim 1, wherein the step of determining includes comparing the detected movement of the second ferromagnetic object with a threshold indicative of clotting.

7. The method of claim 6, further comprising:
   repeating the steps of causing the second ferromagnetic object to move in the second chamber, detecting movement of the second ferromagnetic object, and determining whether the detected movement of the second ferromagnetic object is indicative of clotting until the detected movement of the second ferromagnetic object meets the threshold indicative of clotting.

8. The method of claim 1, further comprising:
   delaying initiation of the step of causing the first ferromagnetic object to move in the first chamber for a predetermined time period after determining that movement of the second ferromagnetic object in the second chamber is indicative of clotting.

9. The method of claim 1, wherein the first and second ferromagnetic objects are identical.

10. The method of claim 1, wherein an outer diameter of the first ferromagnetic object is less than an inner diameter of the first chamber.

11. A non-transitory computer-readable medium programmed with instructions that, when executed, cause a system to carry out the method of claim 1.

12. The method of claim 1, wherein the first ferromagnetic object is has an outer diameter that is at least 25% less than the inner diameter of the first chamber.

13. The method of claim 1, further comprising the step of providing a system including a first chamber and a ferromagnetic object; the system further including:
   a first detector configured to detect a position of the first ferromagnetic object within the first chamber, and
   electronics operably coupled to the first ferromagnetic object and the first detector such that the electronics are configured to control movement of the first ferromagnetic object within the first chamber, wherein the electronics to cause the first ferromagnetic object to move in the first chamber and also to correlate the detected movement of the first ferromagnetic object in the first chamber with clot retraction of the blood.

* * * * *